United States Patent [19]

Mauldin

[11] Patent Number: 4,647,592

[45] Date of Patent: Mar. 3, 1987

[54] START-UP WITH RUTHENIUM CATALYSTS

[75] Inventor: Charles H. Mauldin, Baton Rouge, La.

[73] Assignee: Exxon Research & Engineering Company, Florham Park, N.Y.

[21] Appl. No.: 787,523

[22] Filed: Oct. 15, 1985

Related U.S. Application Data

[63] Continuation-in-part of Ser. No. 568,374, Jan. 5, 1984, abandoned.

[51] Int. Cl.$^4$ ............................................. C07C 1/04
[52] U.S. Cl. ................................... 518/715; 502/325
[58] Field of Search .......................................... 518/715

[56] References Cited

U.S. PATENT DOCUMENTS

| | | | |
|---|---|---|---|
| 3,930,812 | 1/1976 | Harris et al. | 518/711 |
| 3,972,837 | 8/1976 | Acres et al. | 252/473 |
| 4,042,614 | 8/1977 | Vannice et al. | 518/715 |
| 4,088,671 | 5/1978 | Kobylinski | 518/715 |
| 4,089,810 | 5/1978 | Diwell et al. | 252/462 |
| 4,151,190 | 4/1979 | Murchison et al. | 518/715 |
| 4,171,320 | 10/1979 | Vannice et al. | 518/715 |
| 4,199,522 | 4/1980 | Murchison et al. | 260/449 |
| 4,424,282 | 1/1984 | Chauvin et al. | 518/700 |

FOREIGN PATENT DOCUMENTS 1603101  11/1981  United Kingdom .

OTHER PUBLICATIONS

Yoshihiro Kobori et al, Enhancement of the Methanol Formation from CO and $H_2$ Over Supported Ruthenium Catalysts by $H_2$—$H_2O$ Treatment, Chemistry Letters, pp. 553–556, 1983, Japan.

*Primary Examiner*—Howard T. Mars
*Attorney, Agent, or Firm*—Llewellyn A. Proctor

[57] ABSTRACT

A process for the pretreating with steam, steam and carrier gas, steam and hydrogen, or with an oxygen-containing gas, suitably air, a particulate ruthenium catalyst, notably a ruthenium-titania catalyst, for improved start-up in the production of hydrocarbons via carbon monoxide-hydrogen synthesis and methanol conversion reactions.

6 Claims, 1 Drawing Figure

FIGURE
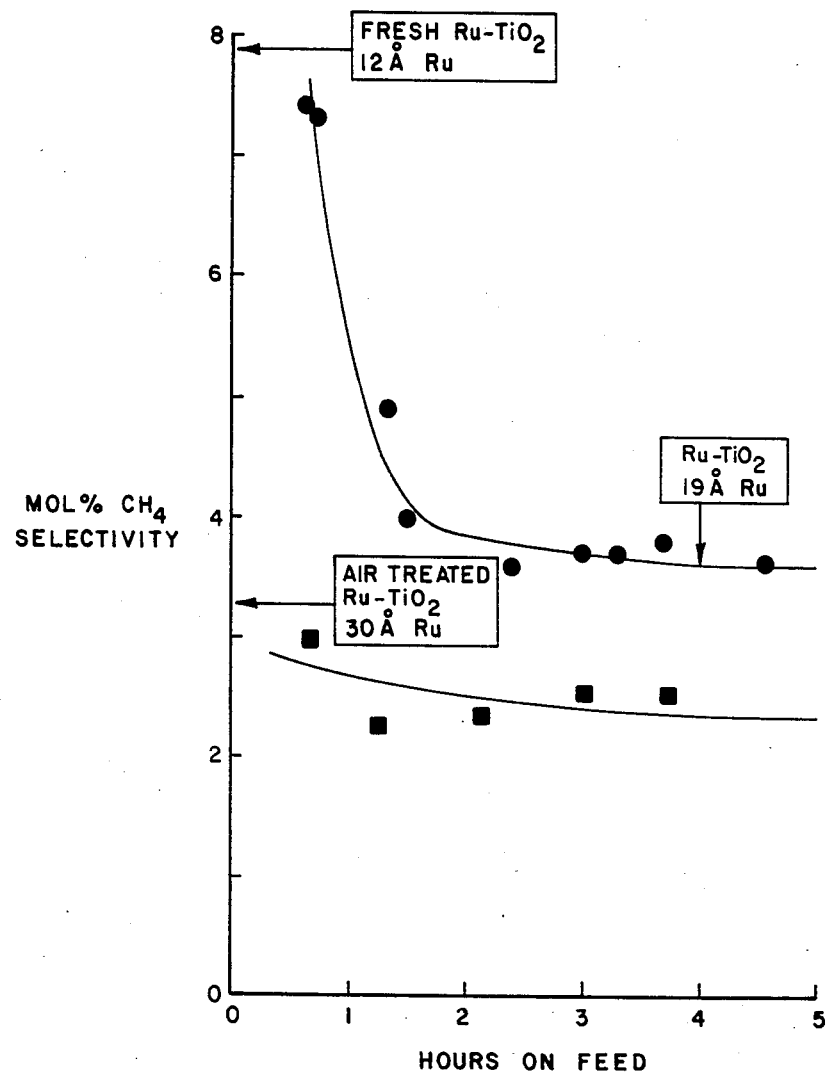

START-UP WITH RUTHENIUM CATALYSTS

RELATED APPLICATION

This is a continuation-in-part of application Ser. No. 568,374, filed Jan. 5, 1984, by Charles H. Mauldin, now abandoned.

BACKGROUND OF THE INVENTION

I. Field of the Invention

This invention relates to improved start-up operations with ruthenium catalysts, especially ruthenium catalysts such as those used in Fischer-Tropsch synthesis, or in methanol conversion to produce hydrocarbons.

II. The Prior Art

Fischer-Tropsch synthesis for the production of hydrocarbons has been known for many years. The use of ruthenium as a catalyst for the production of high-melting hydrocarbon wax from carbon monoxide and hydrogen has been known since the late thirties or early forties. Ruthenium is in limited supply, but on the positive side, ruthenium is known as one of the more active catalysts for use in Fischer-Tropsch synthesis, and its selectivity for making methane in the production of hydrocarbons is relatively low. Moreover, it is recognized as having a low carbon dioxide selectivity. The ruthenium catalyst thus behaves somewhat more ideally than many other catalysts, e.g. iron catalysts, in that more of the hydrogen and carbon monoxide of a synthesis gas are converted to hydrocarbons and water in accordance with the idealized equation: $2H_2 + CO \rightarrow (CH_2)_x + H_2O$; with less of the synthesis gas being converted to carbon dioxide, as in the equation: $H_2 + 2CO \rightarrow (CH_2)_x + CO_2$. The low carbon dioxide selectivity makes use of a ruthenium catalyst for the production of hydrocarbons particularly advantageous for use in processing synthesis gas derived by the conventional technique of steam reforming light hydrocarbon gases, e.g. refinery gas and natural gas. More recently, it has been discovered that ruthenium catalysts are useful for the conversion of methanol to hydrocarbons.

In Exxon Research and Engineering Co.'s U.S. Pat. No. 4,042,614 to Vannice et al which issued Aug. 16, 1977, there is disclosed a ruthenium catalyst, the ruthenium being dispersed on $TiO_2$, other titanium-containing oxides or mixtures of titanium oxides, which provides superior synthesis characteristics in the conversion of carbon monoxide and hydrogen to hydrocarbons, notably olefinic hydrocarbons, particularly $C_2$ to $C_{10}$ olefins. These catalysts, like other ruthenium catalysts, have low methane selectivity, high activity, and low carbon dioxide selectivity. They are also suggested by Vannice et al as having, when treated by contact with air at about 100°–150° C., improved longevity and tolerance to sulfur, and resistance to volatilization in oxidizing atmospheres as contrasted with prior art ruthenium catalysts wherein the ruthenium is supported on other materials, e.g., $Al_2O_3$, $SiO_2$, carbon or the like.

The synthesis of hydrocarbons from carbon monoxide and hydrogen, and conversion of methanol to hydrocarbons over ruthenium catalysts are highly exothermic reactions. Ruthenium-titania catalysts are very active and are capable of providing high conversion at high space velocities with low methane yields. It is essential, however, to temper the extremely high activity exhibited by fresh catalyst, and thereby control the large heat release which leads to high methanation, not only to avoid loss of selectivity in providing the more desirable higher molecular weight hydrocarbons, but also to avoid damage to the catalyst, and to the reactor and auxiliary equipment. Inevitably, to control this heat release on a fresh catalyst, it appears necessary to conduct the synthesis and methanol conversion reactions over a long break-in, or start-up period at low severities. This period generally lasts for several days, during which time the selectivity of the catalyst in producing the more desirable higher molecular weight hydrocarbons is less than optimum. Gradually, over the start-up period however, the selectivity in producing the more desirable higher molecular weight hydrocarbons improves, the severity of the reactions can be gradually increased, and eventually the product stream is optimized in terms of the desired product. The reactor, in terms of production, thus lines out. However, optimization of product yield, requires a long time period with concurrent loss of production. Attempts to cut short this catalyst break-in or start-up period have led to uncontrolled exotherms and eventual catalyst destruction.

OBJECTS

It is, accordingly, the primary objective of the present invention to obviate this disadvantage and others of supported ruthenium catalysts, notably ruthenium-titania catalysts.

A particular object is to provide ruthenium catalysts of improved selectivity for use in synthesis gas and methanol conversion reactions.

A further and more specific object is to provide a new and improved process for the start-up of a reactor which contains a ruthenium catalyst, notably a ruthenium-titania catalyst, as used in Fischer-Tropsch synthesis, or in methanol conversion reactions to produce hydrocarbons.

THE INVENTION

These objects and others are achieved in accordance with the present invention embodying a process for the pretreatment of a particulate catalyst composition comprised of ruthenium, particularly ruthenium dispersed on a titania support, or titania-containing support, by contacting a bed of said catalyst with (1) steam, and preferably steam and a carrier gas, or steam and hydrogen, or (2) an oxygen-containing gas, suitably air, sufficient to mildly agglomerate the ruthenium and form on the particles of catalyst larger agglomerates of ruthenium of average crystallite size ranging from about 15 Å to about 25 Å. Surprisingly, a catalyst pretreated in this manner can be contacted at reaction conditions with a synthesis gas, or with methanol, to produce ab initio the desired higher molecular weight hydrocarbons at good selectivity, and yield, at virtually optimum process conditions without any excessive heat release, excessive methane formation, or fear of run-away exotherms, and without any necessity of a long start-up period, if any. The catalyst "aged" in this manner by the pretreatment, and mild agglomeration of the ruthenium thus eliminates any necessity for the long break-in, or start-up period as is necessary with a fresh, or freshly reactivated ruthenium catalyst. Thus, it has been found that pretreatment of the catalyst in accordance with the process of this invention optimizes the average size of the crystallites of ruthenium of the catalyst to substantially correspond to the average crystallite size of a catalyst at substantially the end of a normal start-up period, which has also been found to range from about 15 Å to about 25 Å.

The steam, steam and carrier gas, or steam and hydrogen, are contacted with the bed of catalyst at temperatures ranging from about 200° C. to about 550° C., preferably from about 230° C. to about 500° C. Preferably both steam and carrier gas, or steam and hydrogen are used. Suitably, the steam and hydrogen are contacted with a bed of fresh, or regenerated, ruthenium catalyst in molar ratio of steam:carrier gas, or steam:hydrogen, ranging from about 20:1 to about 1:100, preferably from about 10:1 to about 1:50, the steam and carrier gas, or steam and hydrogen being admixed, or injected separately into contact with the bed of catalyst.

A partial, mild agglomeration of the ruthenium can also be accomplished by pretreating, or contacting a bed of the catalyst with an oxygen-containing gas, suitably air, at temperatures ranging from about 230° C. to about 400° C., preferably from about 250° C. to about 350° C.

In treating the catalyst either (1) with steam, steam and carrier gas, or steam and hydrogen, or (2) with an oxygen-containing gas, suitably air, pressures are not critical. Suitably, the catalyst is pretreated at pressures ranging from about atmospheric to about 600 pounds per square inch gauge (psig), preferably from atmospheric to about 300 psig. The duration of treatment is dependent to a large extent on the temperature of contact, periods ranging from about 0.5 hour to about 24 hours, or more often from about 2 hours to about 4 hours at the preferred temperatures, these temperatures being satisfactory to produce the mild agglomeration of the ruthenium that is required.

A fresh catalyst, or reactivated catalyst, contains ruthenium of average crystallite size ranging from about 5 Å to about 10 Å, or perhaps about 5 Å to about 12 Å dispersed on a support. In accordance with the process of this invention, a fresh or reactivated catalyst containing ruthenium dispersed on a support in smaller than desired crystallite size is increased by the (1) steam, steam-carrier gas, or steam-hydrogen treatment, or the (2) oxygen-containing gas, or air treatment, to form crystallites of average size ranging from about 15 Å to about 25 Å. In pretreating the ruthenium catalyst in accordance with the process of this invention, ruthenium crystallite sizes of narrow, and quite uniform size distributions can be obtained, particularly by treatment with steam, steam and carrier gas, or steam and hydrogen.

Ruthenium catalysts pretreated in accordance with the process of this invention, can be used in Fischer-Tropsch synthesis reactions to produce from the conversion of carbon monoxide and hydrogen, or by conversion of methanol, products which are predominately $C_{10}+$ linear paraffins and olefins, with very little oxygenates. These catalysts provide, at start-up, significantly better activity and selectivity in the conversion of the carbon monoxide and hydrogen or methanol to hydrocarbons, at similar conditions, than catalysts otherwise similar except that they contain ruthenium crystallites of larger or smaller average size than the catalysts of this invention.

In carrying out a synthesis reaction, the catalyst pretreated in accordance with this invention is formed into a bed, and the bed of catalyst contacted at reaction conditions with a feed comprised of an admixture of carbon monoxide and hydrogen, or compound decomposable in situ within the bed to generate carbon monoxide and hydrogen, to produce a product of middle distillate fuel quality constituted predominately of linear paraffins and olefins. In general, the reaction is carried out at a $H_2$:CO mole ratio ranging from about 0.1 to about 10, preferably from about 0.5 to about 4, at gas hourly space velocities ranging from about 100 $hr^{-1}$ to about 20,000 $hr^{-1}$, preferably from about 300 $hr^{-1}$ to about 2000 $hr^{-1}$, at temperatures ranging from about 150° C. to about 500° C., preferably from about 180° C. to about 300° C., and pressures ranging from about 100 $kP_a$ to about $10^5$ $kP_a$, preferably from about 100 $kP_a$ to about 3100 $kP_a$. The product generally contains 60 percent, and more generally 75 percent or greater, $C_{10}+$ liquid hydrocarbons which boil above 160° C. (320° F.).

In conducting a methanol conversion reaction the partial pressure of methanol within the reaction mixture is generally maintained above about 100 pounds per square inch absolute (psia), and preferably above about 200 psia. It is preferable to add hydrogen with the methanol. Suitably methanol, and hydrogen, are employed in molar ratio of $CH_3OH$:$H_2$ above about 4:1, and preferably above 8:1, to increase the concentration of $C_{10}+$ hydrocarbons in the product. Suitably, the $CH_3OH$:$H_2$ molar ratio, where hydrogen is employed, ranges from about 4:1 to about 60:1, and preferably and methanol and hydrogen are employed in molar ratio ranging from about 8:1 to about 30:1. Inlet hydrogen partial pressures preferably range below about 80 psia, and more preferably below about 40 psia; inlet hydrogen partial pressures preferably ranging from about 5 psia to about 80 psia, and more preferably from about 10 psia to about 40 psia. In general, the reaction is carried out at liquid hourly space velocities ranging from about 0.1 $hr^{-1}$ to about 10 $hr^{-1}$, preferably from about 0.2 $hr^{-1}$ to about 2 $hr^{-1}$, and at temperatures ranging from about 150° C. to about 350° C., preferably from about 180° to about 250° C. Methanol partial pressures preferably range from about 100 psia to about 500 psia, more preferably from about 200 psia to about 400 psia.

It is found that ruthenium supported on titania, or other titania-containing support provides a catalyst which exhibits superior hydrocarbon synthesis characteristics in Fischer-Tropsch reactions, and in methanol conversion reactions. The ruthenium is dispersed on the support in catalytically active amount. Suitably, in terms of absolute concentrations the ruthenium is present in the catalyst composition in amounts ranging from about 0.01 percent to about 8 percent, preferably from about 0.2 percent to about 4 percent, based on the total weight of the catalyst composition (dry basis). These catalyst compositions, it has been found, produce a product which is predominately $C_{10}+$ linear paraffins and olefins, with very little oxygenates. The titania-containing oxide supports used in the practice of this invention are preferably oxides having surface areas of from about 5 to about 150 $m^2g^{-1}$, preferably from about 10 to about 100 $m^2g^{-1}$.

The catalysts employed in the practice of this invention are prepared by techniques known in the art for the preparation of other catalysts. The catalyst can, e.g., be prepared by gellation, or cogellation techniques. Suitably however, ruthenium, or ruthenium and another metal, or metals, if desired, can be deposited on a previously pilled, pelleted, beaded, extruded, or sieved support material by the impregnation method. In preparing catalysts, the ruthenium metal is deposited from solution on the support in preselected amount to provide the desired absolute amount thereof, and if promoters are to be added, the correct weight ratio of each respective metal can be composited with the support. Suitably one metal can be first composited with the support, and then the other; or both may be added simultaneously. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures.

The catalyst, after impregnation, is dried by heating at a temperature above about 25° C., preferably between about 65° C. and 150° C., in the presence of nitrogen or oxygen, or both, in an air stream or under vacuum. The ruthenium metal, or ruthenium metal and another metal, or metals, contained on the catalyst can then be reduced. Reduction is performed by contact of the catalyst with hydrogen or a hydrogen containing gas stream at temperatures ranging from about 175° C. to about 550° C. for periods ranging from about 0.5 to about 24 hours at from about 100 $kP_a$ to about 4000 $kP_a$. A gas containing hydrogen and inert components, or a gas containing hydrogen and carbon monoxide in admixture are satisfactory for use in carrying out the reduction.

The invention will be more fully understood by references to the following demonstrations and examples which present comparative data illustrating its more salient features. All parts are given in terms of weight except as otherwise specified. Feed ratios are expressed as molar ratios of the components.

REFERENCE TO THE DRAWING

The FIGURE graphically illustrates the data given in Table II for Examples 1 and 2, which follow.

EXAMPLES 1 & 2

Degussa P-25 $TiO_2$ was mixed with Sterotex (a vegetable stearine used as a lubricant; a product of Capital City Products Co.), pilled, and ground to 80-150 mesh (Tyler). The support was calcined in air at 500° C. for 4 hours and reduced in $H_2$ at 450° C. for 4 hours to provide a rutile content of about 73% (determined by x-ray diffraction according to the procedure of ASTM D 3720-78).

A 1% Ru-$TiO_2$ catalyst was prepared by impregnating a 495 g. portion of the calcined $TiO_2$ with a solution of 64.3 g. of aqueous ruthenium nitrate solution (7.78 wt. % Ru concentration, supplied by Engelhard Co.) and 450 ml acetone. The solvent was removed with a rotary evaporator and the catalyst dried in a vacuum oven at 120° C.

Portions of the freshly prepared Ru-$TiO_2$ catalyst, initially having ruthenium agglomerates of 12 Å average crystallite size, were contacted in three separate runs in a tubular reactor with synthesis gas, the reactions having been conducted from an initial time "zero" up to 4.6 hours at synthesis conditions of 210° C., 280 psig, GHSV=1000, $H_2/CO=2$. At the end of the period of treatment, in each instance, it was found that the average crystallite size of the ruthenium of a portion of the catalyst employed in a run had increased from 12 Å to approximately 19 Å. No other change in the physical or chemical composition of the catalyst was observed.

An additional portion of the Ru-$TiO_2$ catalyst was treated in air at 0 psig, 500° C. over a period of 3 hours, the average crystallite size of the ruthenium growing from 12 Å to 30 Å. No other change in the physical or chemical composition of the catalyst was observed. This catalyst was also contacted in a tubular reactor with synthesis gas as was the fresh Ru-$TiO_2$ catalyst and at similar conditions. Physical data on each of these catalysts, Catalyst Nos. 1 and 2, respectively, are given in Table 1. In the third and fourth column, respectively, of Table 1, there is listed a description of Catalyst No. 1 prior to its use in making a synthesis run (i.e., a description of the fresh catalyst) and its description at the end of the synthesis run (i.e., the "used" catalyst). A description of the air treated catalyst as it appeared prior to and at the end of the relatively short run is also described as Catalyst No. 2. The ratio of O/Ru was obtained by $O_2$ chemisorption analysis, and the average ruthenium crystallite size was estimated from transmission electron microscope analysis.

TABLE I

| Catalyst No. | Description (1% Ru—$TiO_2$) | O/Ru From $O_2$ Chemisorption | Average Ru Crystallite Size, Å |
|---|---|---|---|
| 1 | Fresh | 1.46 | 12 |
|   | Used, After Short Run[1] | 0.47 | 19 |
| 2 | Air Treated (0 psig, 500° C. - 3 hr.) | 0.54 | 30 |

[1]Conditions of operation: 210° C., 280 psig, GHSV = 1000, $H_2/CO$ = 2.

The results of the synthesis runs made with these catalysts are given in Table II, the runs made with Catalyst No. 1 being identified as Runs "a", "b" and "c," and further identified as "Example 1." The run made with the air treated catalyst is identified as run "d," and is further identified as "Example 2." The third column of Table II gives the % total CO conversion, the fourth column the % CO conversion to hydrocarbons, and the last three columns to the right (Columns 5 through 7) gives the mole % selectivity in terms of $CH_4$, $CO_2$, and $C_2^+$, respectively.

The data are graphically depicted by reference to the FIGURE.

TABLE II

| Run[1] | Time, Hours | % CO Conv. | % CO Conv. to Hydrocarbons | Mole % $CH_4$ | Selectivity $CO_2$ | $C_2^+$ |
|---|---|---|---|---|---|---|
| | | | EXAMPLE 1 Fresh Ru—$TiO_2$ | | | |
| a | 0.6 | 81.0 | 71.6 | 7.4 | 11.6 | 81.0 |
| b | 0.7 | 84.8 | 80.3 | 7.3 | 5.3 | 87.4 |
| b | 1.4 | 94.8 | 90.8 | 4.9 | 4.2 | 90.9 |
| a | 1.5 | 94.4 | 86.3 | 4.0 | 8.6 | 87.4 |
| a | 2.4 | 94.7 | 88.2 | 3.6 | 6.9 | 89.5 |
| c | 3.0 | 98.3 | 89.6 | 3.6 | 8.8 | 87.6 |
| a | 3.3 | 93.1 | 87.8 | 3.7 | 5.7 | 90.6 |
| c | 3.7 | 97.7 | 89.5 | 3.8 | 8.4 | 87.8 |
| a | 4.6 | 92.1 | 87.9 | 3.6 | 4.6 | 91.8 |
| | | | EXAMPLE 2 Air Treated Ru—$TiO_2$ | | | |
| d | 0.7 | 78.6 | 72.1 | 3.0 | 8.3 | 88.7 |
| d | 1.3 | 91.9 | 85.0 | 2.3 | 7.5 | 90.2 |
| d | 2.2 | 94.5 | 88.5 | 2.3 | 6.4 | 91.3 |
| d | 3.0 | 93.7 | 88.6 | 2.5 | 5.4 | 92.1 |
| d | 3.7 | 93.1 | 88.9 | 2.5 | 4.5 | 93.0 |

[1]Conditions of operation: 210° C., 280 psig, GHSV = 1000, $H_2/CO$ = 2.

These data show that the fresh Ru-$TiO_2$ catalyst produces entirely too much methane, but that by the time the average crystallite size of the ruthenium has grown to about 19 Å methane production has dropped from <8 mole % to less than about 4 mole %. An additional run showed that after about 70 hours methane production lines-out, this occurring at about the time the average crystallite size of the ruthenium as reached about 25 Å. As shown in Example 2, when the average crystallite size approximates, or equals 30 Å, methane production is further reduced to a value of about 2.5 mole percent. These data establish that there is a relationship between ruthenium crystallite size and methane selectivity. The larger the average crystallite size of the ruthenium, the lower the methane selectivity. However, it has also been found that when the ruthenium crystallite size becomes too large, the activity maintenance of the catalyst will be debited.

The following example shows that water or steam, or admixtures of steam and hydrogen, can also be used to increase the average crystallite size of the ruthenium, and consequently is also useful in the practice of this invention for pretreatment of a catalyst for use in syn gas operations.

EXAMPLE 3

Several similar portions of a fresh $Ru-TiO_2$ catalyst (1% $Ru-TiO_2$), having ruthenium agglomerates of 12 Å average crystallite size, were contacted in a quartz tube with admixtures of steam and hydrogen at varying conditions, and the ruthenium of the catalyst agglomerated at the conditions given in Table III. These portions of catalyst are referred to as "Catalyst Nos. 3-6 in Table III, the fresh catalyst being identified in Table III as "Catalyst No. 1." Catalyst Nos. 3 and 4 are representative of the fresh $Ru-TiO_2$ catalyst which has been treated by contact with an admixture of steam and hydrogen, and Catalyst Nos. 5 and 6 are representative of portions of the fresh catalyst which have been steam treated (3% $H_2O$ in $N_2$).

In the table, at the third and fourth column, respectively, there is listed for each catalyst on completion of the described treatment the ratio of O/Ru obtained by $O_2$ chemisorption analysis, and the average ruthenium crystallite size estimated from transmission electron microscope analysis and/or $O_2$ chemisorption analysis. The data show that the optimum crystallite sizes can be readily obtained by treatment with dilute steam, steam and carrier gas, or steam and hydrogen.

TABLE III

| Catalyst No. | Description (1% Ru—$TiO_2$) | O/Ru From $O_2$ Chemisorption | Average Ru Crystallite Size, Å |
|---|---|---|---|
| 1 | Fresh | 1.46 | 12 |

TABLE III-continued

| Catalyst No. | Description (1% Ru—$TiO_2$) | O/Ru From $O_2$ Chemisorption | Average Ru Crystallite Size, Å |
|---|---|---|---|
| 3 | $H_2O$ Treated (9:1 $H_2O/H_2$, 280 psig, 300° C. - 4 hrs.) | 1.08 | 15 |
| 4 | $H_2O$ Treated (9:1 $H_2O/H_2$, 280 psig, 230° C. - 16 hrs.) | 0.88 | 18 |
| 5 | $H_2O$ Treated (3% $H_2O$ in $N_2$, 0 psig, 500° C. - 3 hrs.) | 0.98 | 16 |
| 6 | $H_2O$ Treated (3% $H_2O$ in $N_2$, 0 psig, 500° C. - 3 hrs.) | 0.82 | 20 |

It is apparent that various modifications and changes can be made without departing the spirit and scope of the present invention.

What is claimed is:

1. In a process for the conversion of synthesis gas to hydrocarbons by contacting at reaction conditions a feed characterized as an admixture of carbon monoxide and hydrogen with a bed of particulate ruthenium catalyst constituted of a catalytically active amount of ruthenium composited with titania, or a titania-containing support, the improvement comprising
contacting and pretreating the catalyst, prior to initiating the conversion reaction, with an admixture of steam and a carrier gas or an admixture of steam and hydrogen at temperatures ranging from about 200° C. to about 550° C. sufficient to mildly agglomerate and ruthenium and form on the particles of catalyst larger agglomerates of ruthenium of average crystallite size from about 15 Å to about 25 Å approximating that obtained on completion of the startup portion of a synthesis gas operating run.

2. The process of claim 1 wherein the pretreatment temperature ranges from about 230° C. to about 500° C.

3. The process of claim 1 wherein the steam and hydrogen used to pretreat the catalyst are employed in molar ratio of steam:carrier gas or steam:hydrogen ranging from about 20:1 to about 1:100.

4. The process of claim 3 wherein the molar ratio of steam:carrier gas or steam:hydrogen ranges from about 10:1 to about 1:50.

5. The process of claim 3 wherein the catalyst is pretreated at pressures ranging from atmospheric to about 600 psig.

6. The process of claim 5 wherein the catalyst is pretreated at pressures ranging from atmospheric to about 300 psig.

* * * * *